United States Patent
Rajan et al.

[19]

[11] Patent Number: 5,869,771
[45] Date of Patent: Feb. 9, 1999

[54] MULTI-PHASE FLUID FLOW MEASUREMENT APPARATUS AND METHOD

[75] Inventors: Varagur Srinivasa V. Rajan, Sherwood Park; Rodney Keith Ridley, Edmonton, both of Canada

[73] Assignee: Alberta Research Council, Canada

[21] Appl. No.: 740,015

[22] Filed: Oct. 23, 1996

[30] Foreign Application Priority Data

Sep. 18, 1996 [CA] Canada ................................ 2,185,867

[51] Int. Cl.$^6$ ........................................................ G01F 1/74
[52] U.S. Cl. ........................................................ 73/861.04
[58] Field of Search .......................... 73/861.04, 861.02, 73/64.53

[56] References Cited

U.S. PATENT DOCUMENTS

| | | |
|---|---|---|
| 3,176,511 | 4/1965 | Widmyer . |
| 4,168,624 | 9/1979 | Pichon . |
| 4,203,935 | 5/1980 | Hackenjos . |
| 4,441,361 | 4/1984 | Carlson et al. . |

(List continued on next page.)

FOREIGN PATENT DOCUMENTS

| | | | |
|---|---|---|---|
| 911203 | 10/1972 | Canada | .................................. 73/125 |
| 1134174 | 10/1982 | Canada . | |
| 2063820 | 1/1991 | Canada . | |
| 2103254 | 9/1993 | Canada . | |
| 2128756 | 5/1984 | United Kingdom . | |

OTHER PUBLICATIONS

*Perry's Chemical Engineers Handbook,* 6th Ed., McGraw–Hill Book Company, pp. 18–19, 18–20, 18–22 and 18–25, Robert H. Perry (Editor).
*Chemical Engineering,* vol. 2 Unit Operations by J.M. Coulson and J.F. Richardson, 1962, Pergamon Press, pp. 21–24.
Jaeger Tri–Packs, Inc. advertising materials and product bulletins dated Aug. 12, 1994 entitled "Tri–Packs—The Most Efficient and Cost Effective Column Packing", 4 pages.
Kay–Ray/Sensall Inc. materials, undated, entitled "Kay–Ray Non–Contacting Measurement Systems," 4 pages.
Rajan, V.S.V., Ridley, R.K. and Rafa, K.G., "Multiphase Flow Measurement Techniques—A Review", J. Energy Resources Technology, vol. 115, No. 3, pp. 151–161 (1993).

(List continued on next page.)

*Primary Examiner*—Richard Chilcot
*Assistant Examiner*—Jewel Artis
*Attorney, Agent, or Firm*—Wendy K. Buskop; Chamberlain, Hrolicka et al.

[57] ABSTRACT

The invention is an apparatus and a method for characterizing the flow of a multi-phase fluid. The apparatus is comprised of: a conduit having a first end and a second end, for flowing the fluid from the first to the second ends, and a first point and a second point located between the first and second ends; a mixer for mixing the fluid as it flows from the first to the second ends such that the fluid is substantially homogeneous at the first point and such that the substantial homogeneity of the fluid is maintained between the first and second points; and means for determining at least one of a volumetric flow rate of the substantially homogeneous fluid at a first location in the conduit between the first and second points and a density of the substantially homogeneous fluid at a second location between the first and second points. The method is comprised of the steps of: mixing the fluid as it flows from the first to the second ends of the conduit such that the fluid is substantially homogeneous at the first point and such that the substantial homogeneity of the fluid is maintained between the first and second points; and determining at least one of the volumetric flow rate of the substantially homogeneous fluid at the first location and the density of the substantially homogeneous fluid at the second location.

30 Claims, 2 Drawing Sheets

U.S. PATENT DOCUMENTS

| | | | |
|---|---|---|---|
| 4,753,106 | 6/1988 | Brenner et al. | 73/29 |
| 4,815,536 | 3/1989 | Prendergast et al. | 166/250 |
| 4,829,831 | 5/1989 | Kefer et al. | 73/861.02 |
| 4,856,344 | 8/1989 | Hunt . | |
| 4,974,452 | 12/1990 | Hunt et al. | 73/861.04 |
| 5,190,103 | 3/1993 | Griston et al. | 73/861.04 |
| 5,400,657 | 3/1995 | Kolpak et al. | 73/861.04 |
| 5,501,099 | 3/1996 | Whorff | 73/961.04 |

OTHER PUBLICATIONS

Hayward, A.T.J. "In–Line Mixing Devices", International Oyez–IBC Ltd. Conference on Recent Developments in the Custody Transfer Measurement of Crude Oil, London, U.K. (Nov. 3–4, 1982) pp. 99–109, 111–116.

Martin, W.W., Woiceshyn G.E. and Torkildsen, B.H. "A Proven Oil/Water/Gas Flow Meter for Subsea" presented at the 23rd annual OTC in Houston, Texas May 6–9, 1991 (20 pages).

"Tri–Packs Column Packing", Catalogue, Fabco Plastics, Section 8, p. 34, Buyer's Guide (1990–91).

MULTI-PHASE FLUID FLOW MEASUREMENT APPARATUS AND METHOD

This application claims priority from Canadian application serial number 2,185,867 filed Sep. 18, 1996 currently pending.

1. Technical Field

The present invention relates to a method and an apparatus for characterizing the flow of a multi-phase fluid, including determining at least one of a volumetric flow rate and a density for the fluid.

2. Background Art

The characterization or measurement of the flow of a multi-phase fluid presents numerous difficulties. A multi-phase fluid is a fluid having more than one phase (liquid or gas), such as a fluid having two or more liquid phases or a combination of a gas phase with one or more liquid phases. Attempts have been made to overcome these difficulties given the recognized need in industrial applications for the accurate characterization or measurement of the flow of such multi-phase fluids. For example, the oil and gas industry requires accurate measurement of the production of multi-phase fluids, comprising oil, hydrocarbon gases, water and/or other associated fluids, from underground reservoirs through wells in order that the production from each well can be assessed, managed and allocated in a reliable and consistent manner. In addition to the oil and gas industry, similar needs exist in other industries such as the chemical industry.

Generally, measurement of the flow of a multi-phase fluid presents difficulties due to the wide variety of flow regimes which are possible, general flow instability and the likelihood of a slip between the phases of the fluid due to segregation. For example, in a production well, the multi-phase fluid is likely comprised of oil, water and hydrocarbon gas. A slip may occur between the oil and water resulting in the production of separate slugs or plugs of oil and water. Meanwhile, the gas may take the form of small bubbles, large slugs of gas or a discrete layer of gas above the water and oil. A slip may also occur between the liquid phase and the gas phase and is more likely.

The conventional approach of industry to the characterization of multi-phase fluid flows is fluid sampling and separation. A sample of the multi-phase fluid is diverted from the flow and allowed to separate into its component phases. Once separated, measurements may be made of the individual phases using conventional single-phase flow measurement techniques and devices. This conventional approach has several drawbacks. Sampling requires the extraction of a quantity of the fluid, on either a continuous or a periodic basis, by an intrusive sampling probe. As well, homogenization of the flow may be required prior to sampling in order to obtain a representative sample of the fluid. Further, sampling and separation of the phases may be time consuming and the required equipment may be costly, bulky, complex and require ongoing maintenance. Thus, the efficiency and economics of conventional field fluid samplers and separators have not been found to be completely satisfactory.

Alternatively, Canadian Patent No. 1,134,174 issued Oct. 26, 1982 to Rhodes et al is directed at a device which measures the flow of a multi-phase fluid without sampling and separation of the phases. Rhodes describes a flow meter which is designed to measure the individual flow rates of the phases of the fluid by measuring a frictional pressure drop and an accelerational pressure drop of the fluid. The frictional pressure drop is measured across a twisted tape in a conduit carrying the flow, while the accelerational pressure drop is measured across a venturi positioned in the conduit downstream of the twisted tape. However, this device does not completely address the problems associated with the variable flow regimes, flow instability and slip in multi-phase fluid flows.

However, specific attempts have been made to address these problems as shown by Canadian Patent Application No. 2,103,254 filed by Farchi et al and published Sep. 18, 1993, U.S. Pat. No. 3,176,511 issued Apr. 6, 1965 to Widmyer, U.S. Pat. No. 4,168,624 issued Sep. 25, 1979 to Pichon, U.S. Pat. No. 4,441,361 issued Apr. 10, 1984 to Carlson et al, U.S. Pat. No. 4,856,344 issued Aug. 15, 1989 to Hunt, U.S. Pat. No. 4,974,452 issued Dec. 4, 1990 to Hunt et al and U.S. Pat. No. 5,190,103 issued Mar. 2, 1993 to Griston et al.

Farchi describes an apparatus for measuring the flow rates of the gas and liquid components of a fluid in a series flow path. Farchi states that the velocity ratio between the gas and the liquid in the series flow path is preferably maintained at a known value, such as one, by using either a first and second mixer or a positive displacement flow meter. The first and second mixers are coupled at the input and output of the volumetric flow meter. However, the specific method by which the velocity ratio is effectively maintained at one through the volumetric flow meter is not described. Further, no definition or description of the positive displacement flow meter, or the method by which it maintains the velocity ratio, is provided by Farchi.

Widmyer provides for a measuring apparatus which includes a plurality of baffle plates which form the walls of a tortuous passageway for the fluid. The fluid passes through the passageway, where it is mixed, and subsequently through a partition and into a separate fluid density measuring device. The fluid then passes through a second partition into a separate flow rate or volume measuring device. Similarly, each of Pichon, Carlson, Hunt, Hunt et al and Griston all describe devices which discuss the use of a mixer or other means, for making the fluid flow substantially uniform, which mixer is located upstream of the particular measuring devices or flow meters used in each device.

Each of these patents describe the mixing of the flow of the multi-phase fluid prior to the taking of any measurements so that the fluid may subsequently be measured by means suitable for a single-phase fluid. However, although these patents attempt to address the problems of varying flow regimes, flow instability and slip, these problems may not be completely overcome by the devices and techniques disclosed by these patents.

As stated, all of the devices and techniques disclosed by these patents attempt to achieve uniformity in the flow of the multi-phase fluid before measuring it by mixing the segregated phases. However, partial re-segregation or separation of the phases will occur immediately following cessation of the mixing of the phases, or once the fluid has passed through the mixer, due to the immiscibility and differences in the densities (buoyancy or gravity segregation effect) of the fluid phases. Thus, the fluid flow subsequently measured by each of the disclosed measuring devices is not uniform or homogeneous, but rather, it is partially or completely segregated or separated into its component phases. This partial or complete segregation of the phases of the fluid flow can cause inaccuracies in the measurements being made, particularly when using measurement devices and techniques conventionally used for single-phase fluids. Conventional single-phase fluid flow measurement devices and techniques are feasible and provide relatively accurate measurements only when the multi-phase fluid flow is homogeneous or substantially uniform.

There is therefore a need in the industry for an improved method and an improved apparatus for relatively accurately characterizing the flow of a multiphase fluid. As well, there is a need for a method and a device capable of characterizing the multi-phase fluid flow using conventional single-phase fluid flow measuring devices and techniques. Further, the device is preferably relatively compact and simple and relatively economical and easy to construct and use in the field.

DISCLOSURE OF INVENTION

The present invention relates to a method and an apparatus for characterizing the flow of a multi-phase fluid in a relatively accurate manner as compared to known methods and apparatuses. Further, the invention relates to a method and an apparatus which provide for the simultaneous or concurrent mixing and measuring of the multi-phase fluid flow to characterize it. By continuously mixing the multi-phase fluid flow during the measurement of it, the within invention permits conventional single-phase fluid flow measuring devices and techniques to be used, while still obtaining relatively accurate measurements for characterization of the multi-phase fluid flow.

In the method form of the invention, the invention is comprised of a method for characterizing the flow of a multi-phase fluid as the fluid flows through a conduit from a first end of the conduit to a second end of the conduit, the method comprising the steps of:

(a) mixing the fluid as it flows from the first end to the second end such that the fluid is substantially homogeneous at a first point in the conduit and such that the substantial homogeneity of the fluid is maintained between the first point and a second point in the conduit, wherein the first point and the second point are located between the first end of the conduit and the second end of the conduit; and (c) determining at least one of a volumetric flow rate of the substantially homogeneous fluid at a first location in the conduit between the first point and the second point and a density of the substantially homogeneous fluid at a second location in the conduit between the first point and the second point.

The mixing step is preferably comprised of continuously mixing the fluid as it flows from the first end to the second end. The mixing step may be accomplished or performed by any known mixing process or device, or a combination of two or more such processes or devices, able to produce the substantially homogeneous fluid at the first point and to maintain the substantial homogeneity of the fluid between the first and second points in the conduit. However, preferably, the mixing step is comprised of directing the fluid through at least one in-line mixer located in the conduit. Further, the in-line mixer is preferably comprised of a static mixer.

In the preferred embodiment, the in-line mixer, being a static mixer, extends substantially between the first and second ends of the conduit. Preferably, the static mixer is comprised of the conduit containing a packing material for disrupting the flow of the fluid through the conduit. The packing material may be comprised of a plurality of permeable ellipsoidal bodies.

Further, throughout the mixing and determining steps, the first and second points in the conduit may be at different elevations. Where the fluid is comprised of a liquid continuous medium, the first point is preferably below the second point. Where the fluid is comprised of a gas continuous medium, the first point is preferably above the second point. In either case, in the preferred embodiment, the first and second points are aligned such that the fluid flows substantially vertically from the first point to the second point in the conduit.

The volumetric flow rate determining step may be achieved or performed by any known device or process, or a combination of two or more such processes or devices, for determining volumetric flow rate as long as it is compatible with, and suitable for, the specific nature and properties of the fluid being measured. Further, because the mixer produces a substantially homogeneous multi-phase fluid flow, any known process or device, or combination of two or more processes and devices, for determining the volumetric flow rate of a single-phase fluid may be used as long as it is compatible with, and suitable for, the specific nature and properties of the homogeneous fluid being measured.

Preferably, the volumetric flow rate determining step is comprised of the steps of:

(a) measuring a pressure drop of the fluid at the first location in the conduit, wherein the fluid has a flow pattern at the first location which causes the pressure drop; and (b) using the pressure drop at the first location to determine the volumetric flow rate of the fluid at the first location in the conduit.

The flow pattern of the fluid at the first location may be created by any known technique, process or device. However, the flow pattern of the fluid is preferably created by the in-line mixer, preferably being a static mixer, and the measuring step is comprised of measuring the pressure drop across the static mixer at the first location.

The density determining step may be performed using one or more of any known type of density measuring device, which may be comprised of an on-line density measuring device or an off-line density measuring device as long as it is compatible with, and suitable for, the specific nature and properties of the fluid being measured. Further, because the multi-phase fluid is substantially homogenized by the mixer, any known device, or combination of devices, for determining the density of a single-phase fluid may be used as long as it is compatible with, and suitable for, the specific nature and properties of the homogeneous fluid being measured. Preferably, the density determining step is performed using an on-line density measuring device comprising a nuclear radiation or gamma densitometer.

Finally, when the determining step is comprised of determining the volumetric flow rate and the density of the substantially homogeneous fluid, the method may be further comprised of the step of combining the density with the volumetric flow rate in order to determine a mass flow rate for the fluid.

In the apparatus form of the invention, the invention is comprised of an apparatus for characterizing the flow of a multi-phase fluid, the apparatus comprising:

(a) a conduit having a first end and a second end, for flowing the fluid from the first end to the second end, and a first point and a second point located between the first end of the conduit and the second end of the conduit;

(b) a mixer for mixing the fluid as it flows from the first end to the second end such that the fluid is substantially homogeneous at the first point and such that the substantial homogeneity of the fluid is maintained between the first point and the second point in the conduit; and (c) means for determining at least one of a volumetric flow rate of the substantially homogeneous fluid at a first location in the conduit between the first point and the second point and a density of the substantially homogeneous fluid at a second location between the first point and the second point.

The mixer preferably continuously mixes the fluid as it flows from the first end to the second end. Further, the mixer may be any known type of mixing device, or a combination of two or more such mixing devices, able to mix the fluid in a manner to produce the substantially homogeneous fluid at the first point and to maintain the substantial homogeneity of the fluid between the first and second points. However, the mixer is preferably comprised of at least one in-line mixer located in the conduit. Further, the in-line mixer is preferably a static mixer.

In the preferred embodiment, the in-line mixer, being a static mixer, extends substantially between the first and second ends of the conduit. Preferably, the static mixer is comprised of the conduit containing a packing material for disrupting the flow of the fluid through the conduit. The packing material may be comprised of a plurality of permeable ellipsoidal bodies.

The volumetric flow rate determining means may be any known type of device, or combination of devices, for determining volumetric flow rate as long as it is compatible with, and suitable for, the specific nature and properties of the fluid being measured. Further, because the muitl-phase fluid is substantially homogenized by the mixer, any known device, or combination of devices, for determining the volumetric flow rate of a single-phase fluid may be used as long as it is compatible with, and suitable for, the specific nature and properties of the homogeneous fluid being measured. In the preferred embodiment, the volumetric flow rate determining means is comprised of a measuring device for measuring a pressure drop of the fluid at the first location in the conduit, wherein the fluid has a flow pattern at the first location which causes the pressure drop.

The flow pattern of the fluid at the first location may be created by any known technique, process or device. However, the flow pattern of the fluid is preferably created by the in-line mixer, preferably being a static mixer, such that the measuring device measures the pressure drop across the static mixer at the first location. In this preferred case, the measuring device may be comprised of any known measuring device or devices capable of measuring the pressure drop, such as a differential pressure device.

As well, the density determining means may be comprised of one or more of any known type of density measuring device, including an on-line density measuring device or an off-line density measuring device, as long as it is compatible with, and suitable for, the specific nature and properties of the fluid being measured. Further, because the multi-phase fluid is substantially homogenized by the mixer, any known device, or combination of devices, for determining the density of a single-phase fluid may be used as long as it is compatible with, and suitable for, the specific nature and properties of the homogeneous fluid being measured. However, preferably, the density determining means is comprised of an on-line density measuring device comprising a nuclear radiation or gamma densitometer.

Finally, when the on-line density measuring device is comprised of a nuclear radiation or gamma densitometer, the apparatus, including the conduit, may be adapted to minimize interference of the apparatus with the measurement of the density. For instance, the conduit may comprise a sealed window at the second location to minimize interference by the conduit. Further, the ellipsoidal bodies contained in the conduit in the preferred embodiment may be comprised of plastic to minimize interference by the ellipsoidal bodies with the nuclear radiation.

BRIEF DESCRIPTION OF DRAWINGS

Embodiments of the invention will now be described with reference to the accompanying drawings, in which.

BEST MODE OF CARRYING OUT INVENTION

The within invention is comprised of both a method and an apparatus (20) for characterizing the flow of a multi-phase fluid (22). In the preferred embodiment, the flow of the multi-phase fluid (22) is characterized by determining at least one of a volumetric flow rate and a density of the fluid (22), and preferably both.

A multi-phase fluid (22) is a fluid having more than one phase (liquid or gas), such as a fluid having two or more liquid phases or a combination of a gas phase with one or more liquid phases. The constituent phases of the multi-phase fluid (22) may be separated into distinct layers or inter-mixed in a manner such that there may be separate or discrete slugs or plugs of the various liquid phases or bubbles or slugs of the various gas phases co-mingled together. Preferably, the multi-phase fluid (22) either includes no solid particles or includes an amount or size of solid particles which do not substantially inhibit the flow of the fluid (22) through the apparatus (20).

Figure 1:
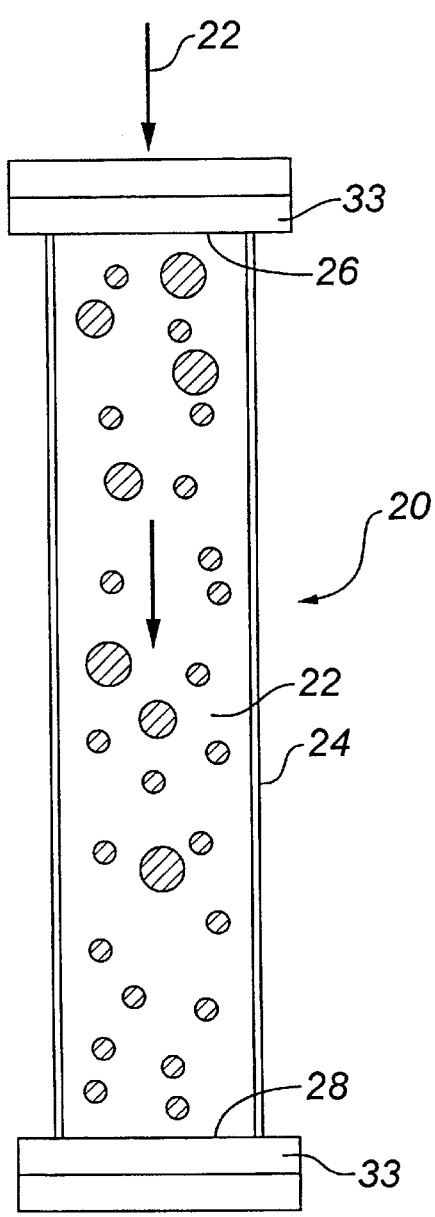
FIG. 1 is a schematic representation of a gas continuous medium in the preferred embodiment of the apparatus.
Figure 2:
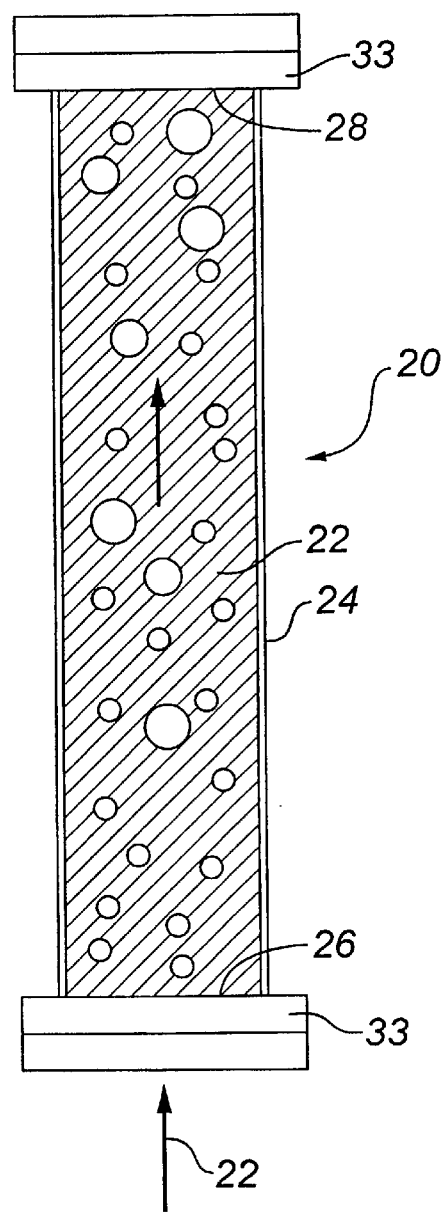
FIG. 2 is a schematic representation of a liquid continuous medium in the preferred embodiment of the apparatus.
Figure 3:
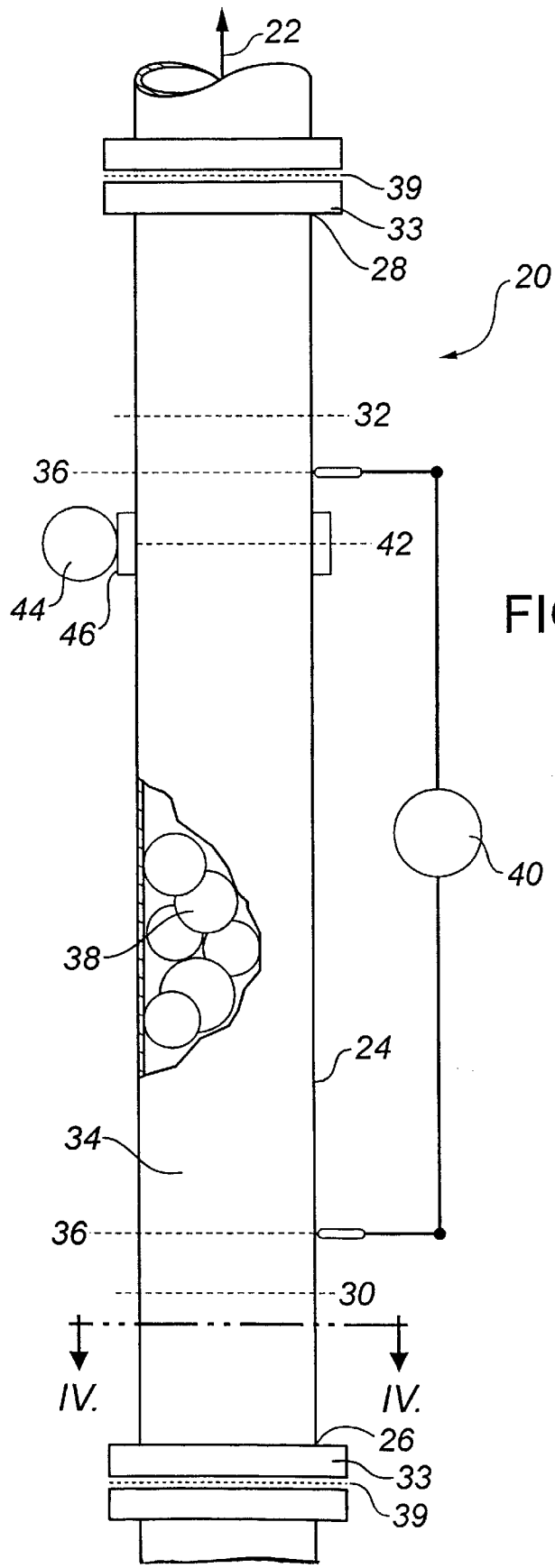
FIG. 3 is a side view of the preferred embodiment of the apparatus having a cut-away portion.
Figure 4:
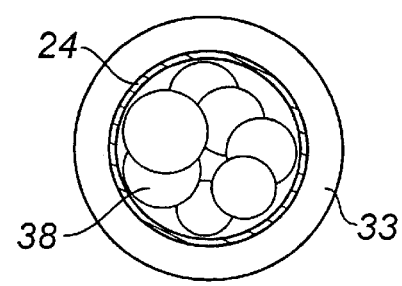
FIG. 4 is a cross-section of the apparatus of FIG. 3 taken along lines 4—4.

Further, the fluid (22) may be either a gas continuous medium or a liquid continuous medium, as represented in FIGS. 1 and 2 respectively. A gas continuous medium is defined as a multi-phase fluid flow medium wherein the continuous fluid phase is a gas into which the other phases (i.e. liquid droplets and solid particles, if present) are dispersed. A liquid continuous medium is defined as a multi-phase fluid flow medium wherein the continuous fluid phase is a liquid into which the other phases (i.e. gas bubbles and solid particles, if present) are dispersed. The dispersed or distributed phase is also termed as the discontinuous phase. In the preferred embodiment, the composition of the fluid (22) is either a gas continuous or a liquid continuous medium. Further, the flow of the fluid (22) may be an annular dispersed flow such that either a liquid film annulus or a gas film annulus may be present depending upon whether the fluid (22) is a gas continuous medium or a liquid continuous medium respectively.

Referring to FIGS. 1 and 2, the apparatus (20) is comprised of: a conduit (24), having a first end (26) and a second end (28), for flowing the fluid (22) therethrough from the first to the second ends (26, 28), and a first point (30) and a second point (32) located between the first and second ends (26, 28); and a mixer (34) for mixing the fluid (22) as it flows from the first to the second ends (26, 28) such that the fluid (22) is substantially homogeneous at the first point (30) and such that the substantial homogeneity of the fluid (22) is maintained between the first and second points (30, 32). The first point (30) is located nearer the first end (26) than the second point (32), while the second point (32) is located nearer the second end (28) than the first point (30). Further, the longitudinal axis of the conduit (24) extending between the first and second ends (26, 28) is preferably straight, without any bends, angles or curves.

The first end (26) of the conduit (24) is defined by the point at which the mixing of the fluid (22) commences. Due to a mixing entrance effect, when the mixing of the fluid (22) commences, the fluid (22) is not immediately substantially homogeneous. Rather, the fluid (22) must undergo a period of mixing in order to achieve a substantially homogeneous state. As a result, the first end (26) of the conduit (24), at which the mixing commences, must be located a sufficient distance upstream of the first point (30) to take into account the mixing entrance effect and to allow the mixing to act on the fluid flow and thereby produce the substantially homogeneous fluid at the first point (30).

The second end (28) of the conduit (24) is defined by the point at which the mixing of the fluid (22) is able to cease and yet still produce the substantially homogeneous fluid between the first and second points (30, 32). Due to a mixing exit effect, the substantial homogeneity of the fluid (22) may not be maintained for a distance upstream of the point at which the mixing actually ceases. As a result, the second end (28), at which the mixing of the fluid (22) ceases, must be located a sufficient distance downstream from the second point (32) to take into account the mixing exit effect and thereby maintain the substantial homogeneity of the fluid (22) between the first and second points (30, 32).

The conduit (24) is defined by the distance between the first and second ends (26, 28). The minimum length of the conduit (24) is governed by the need to provide the fluid (22) with sufficient residence time within the conduit (24) to permit mixing of the fluid (22) such that it is substantially homogeneous at the first point (30) and between the first and second points (30, 32) and to permit characterization of the substantially homogeneous fluid by the characterizing means described below. The maximum length of the conduit (24) is governed primarily by the maximum permissible pressure drop between the ends (26, 28) of the conduit (24). The conduit (24) is preferably cylindrical in cross-section and its diameter must be selected to permit the flow of the fluid (22) through the conduit (24) without causing significant backup in the flow or excessive pressure drop and to provide sufficient space within the conduit (24) for containing other elements of the apparatus (20), as described below. As a result, both the diameter and the length of the conduit (24) are dependent upon the volumetric flow rate of the fliuid (22) through the conduit (24) and upon the composition and other characteristics of the fluid (22).

Generally, the overall design of the preferred embodiment of the apparatus (20), including each constituent element such as the conduit (24), are dependent upon the composition and other characteristics of the fluid (22), the fluid flow rate and the desired pressure drop of the fluid (22) in the apparatus (20), as discussed further below. Specifically, based upon these variables, the preferred embodiment, and the parameters and specifications of its elements, are designed in order to achieve the desired results, as described below.

The conduit (24) may be comprised of any erosion and corrosion-resistant material capable of withstanding the pressure of the fluid (22) within the conduit (24) and which will not interfere with the characterization of the fluid flow by the apparatus (20). In the preferred embodiment, the conduit (24) is comprised of a steel pipe. However, the specific material requirements of the conduit (24) will vary depending upon the characteristics and nature of the fluid (22) flowing therethrough.

The conduit (24) may be connected into the flow of the fluid (22) by any suitable means. However, in the preferred embodiment, a connector flange (33) is located at each of the first and second ends (26, 28). Depending upon the specific connector flange (33) being used, the diameter of the conduit (24) may decrease or increase slightly at or near either or both of the first and second ends (26, 28) in order that the conduit (24) may be more easily connected into the fluid (22) flow. Preferably, the reduction or enlargement in the diameter occurs gradually in order to decrease the effect of the changed diameter on the flow of the fluid (22).

As stated, the mixer (34) mixes the fluid (22) in the conduit (24) such that the fluid (22) is substantially homogeneous over the cross-section of the conduit (24) at the first point (30) and such that the substantial homogeneity of the fluid (22) is maintained over the cross-section of the conduit (24) between the first point (30) and the second point (32) in the conduit (24). The homogeneity is maintained by the mixer (34) continuously mixing the fluid (22) as it flows from the first to the second ends (26, 28). The fluid (22) is considered to be substantially homogeneous when the mixing variation coefficient (omega/x*) of the fluid is 0.05 or less, where "omega" is the standard deviation of the concentration "x" (concentration distribution over the section being considered) of one phase in the fluid (22) and "x*" is the mean concentration.

As well, the apparatus (20) is further comprised of means for determining at least one of the volumetric flow rate and the density of the substantially homogeneous fluid. Preferably, the apparatus (20) includes means for determining both the volumetric flow rate and the density. The volumetric flow rate determining means determine the volumetric flow rate of the substantially homogeneous fluid at a first location 136) in the conduit (24). The density determining means determine the density of the substantially homogeneous fluid at a second location (42) in the conduit (24). Both the first location (36) and the second location (42) are located between the first and second points (30, 32). Thus, the apparatus (20) provides for the simultaneous or concurrent mixing and characterizing of the fluid (22). The volumetric flow rate and the density of the fluid (22) are determined at locations in the conduit (24) at which the mixer (34) has caused and maintains the substantially homogeneity of the fluid (22).

The mixer (34) may be comprised of any known type of mixing device, or a combination of one or more such devices, capable of producing and maintaining the substantially homogeneous fluid (22) between the first and second points (30, 32) in the conduit (24). Therefore, the mixer (34) must be compatible with the specific nature and properties of the fluid (22) being mixed. Preferably, the mixer (34) is an in-line mixer located within, or substantially within, the conduit (24) in a manner and at a location within the conduit (24) to produce the substantially homogeneous fluid at the first point (30) and between the first and second points (30, 32). Further, the in-line mixer is preferably a static mixer due to the relative simplicity, energy efficiency and cost effectiveness of static mixers as compared to other mixers.

In the preferred embodiment, the static mixer (34) extends substantially between the first end (26) and the second end (28) of the length of conduit (24). As a result, the mixer (34) mixes the fluid (22) continuously from the first to the second ends (26,28). The mixer (34) thereby achieves substantial homogeneity of the fluid (22) at the first point (30) and maintains substantial homogeneity of the fluid (22) as it flows from the first to the second points (30, 32), and thus, at the first and second locations (36, 42). Although not preferred, a gap in the mixer (34), being an area between the first and second ends (26, 28) not containing the mixer (34), is permissible as long as the mixing effect from the mixer (34) maintains the substantial homogeneity of the fluid (22) in the gap. In essence, the mixer (34) downstream from the gap produces an upstream mixing effect, while the mixer (34) upstream from the gap produces a downstream mixing effect. The upstream and downstream mixing effects act together to produce a continuous mixing action of the fluid within the gap. Thus, the permissible size of the gap will depend upon the extent of the mixing effects produced by the mixer (34) on either side of the gap.

Further, the static mixer (34) is preferably comprised of the conduit (24) containing a packing material which extends from the first end (26) to the second end (28) of the conduit (24). The packing material allows the fluid (22) to flow therethrough, while creating a tortuous flow path which disrupts the flow of the fluid (22) sufficiently to mix the fluid (22) to a substantially homogeneous state. A mixer (34) comprised of the packing material is preferred because the packing material, and thus the mixer (34), are relatively compact, simple in their structure, and easy and inexpensive to use, maintain and replace, as needed, as compared to other known mixers.

Any packing material may be used which is capable of mixing the fluid (22) in a manner to achieve substantial homogeneity at a wide range of flow rates. Further, the packing material should be chosen so that it is compatible with the fluid (22) and so that the mixing effect caused by it does not result in a permanent change in the fluid flow characteristics or an excessive pressure drop of the fluid (22). As well, the packing material is preferably light weight and rugged. Any suitable configuration of the packing material may be used, including broken solids, shaped packings and grids. However, packing materials with low porosity, low crushing strength or high density are not preferred. In selecting the type, configuration and specific dimensions of the packing material to be used, some of the factors to be considered are as follows: the length and overall dimensions of the conduit (24); the amount and size of any solids in the fluid (22), so that any plugging by the solids is minimized, and other fluid characteristics; the acceptable pressure drop as the fluid (22) passes through the packing material; the flow rate of the fluid (22) through the conduit (24); and the ability to pack the material to provide good packing characteristics.

In the preferred embodiment, the packing material is comprised of a plurality of hollow, permeable, ellipsoidal bodies (38). However, although hollow bodies (38) are used in the preferred embodiment, the bodies (38) need not be hollow as long as the packing material has the characteristics noted above. Further, the bodies (38) may have a shape other than an ellipsoid, such as a rhomboid or a cylinder. However, ellipsoidal bodies (38) are preferred as they permit close packing of the bodies (38) within the conduit (24) and provide a relatively high void space, low blockage tendency, low pressure drop of the fluid (22) passing therethrough, and high active surface area for mixing the fluid (22). Due to the relatively low pressure drop, the ellipsoidal bodies (38) are particularly suited to a wide range of flow rates and the preferred apparatus (20) may be used where excessive pressure drops are likely to be a concern. The ellipsoidal bodies (38) may be made of any suitable material which is compatible with the fluid (22). However, the ellipsoidal bodies (38) are preferably made of plastic as plastic is relatively inexpensive, light weight, compatible with most uses of the apparatus (20) and will not tend to interfere with the equipment used to measure and characterize the fluid (22), as discussed further below. Suitable plastics include polyethylene, polypropylene and polytetrafluorethylene.

The preferred ellipsoidal bodies (38) used in the apparatus (20) are sold under the registered trade-mark TRI-PACKS® by Jaeger Tri-Packs Inc. and are generally described in U.S. Pat. No. 4,203,935 granted May 20, 1980 to Rolf Jaeger. The TRI-PACKS® packing is comprised of spherical bodies shaped in a lattice-work jacket or network of ribs and struts. Although specifically designed as a filter medium, it has been found that the TRI-PACKS® packing may be used in the within invention to effectively mix the fluid (22). The size of the preferred TRI-PACKS® packing will depend upon the diameter of the conduit (24). However, generally, TRI-PACKS® packing having a diameter of about 25 mm, being the smallest size commercially available, is preferred as this size appears to be most versatile. TRI-PACKS® packing having a diameter of 25 mm can typically be used in varying sizes of conduit (24) having larger or smaller diameters.

Further, in the preferred embodiment, a screen (39) is located across the conduit (24) adjacent the connector flange (33) at each of the first and second ends (26, 28) of the conduit (24). The screens (39) are sized to permit the flow of the fluid (22) into and out of the conduit (24) relatively unimpeded while retaining the ellipsoidal bodies (38) within the conduit (24). Further, the screen (39) at the first end (26) may also be selected to filter solid particles of a desired size from the fluid (22) and prevent their entry into the conduit (24).

Although the preferred mixer (34) is described above, as stated, the mixer (34) may be comprised of any known type of mixing device capable of performing the function of the preferred embodiment described herein. Thus, the mixer (34) may be comprised of a rotary mixer, a recirculating jet mixer, other types of static mixer or a variable geometry static mixer. Other types of static mixer include flow diverters, perforated pipes, sieve plates, corrugated plates, helical vanes and the like, which compel the fluid (22) to change direction abruptly and thereby promote turbulence and mixing of the fluid (22). Further, a variable geometry static mixer may be used, if needed, to regulate the disruption of the fluid (22) as the volumetric flow rate of the fluid (22) through the conduit (24) changes.

As well, the mixer (34) may be comprised of a combination of two or more known types of mixing devices which act together to produce the substantially homogeneous fluid between the first and second points (30, 32) in a manner similar to the mixing effect achieved when a gap exists in the mixer (34), as described above. For instance, a first mixer (not shown) may be located adjacent the first point (30) and a second mixer (not shown) may be located adjacent the second point (32). A first downstream mixing effect of the first mixer and a second upstream mixing effect of the second mixer together produce the substantially homogeneous fluid between the first and second points (30, 32). The first and second mixing effects combine to result in a continuous mixing of the fluid (22) between the first and second points (30, 32). Thus, the acceptable distance between the first and second mixers will be dependent upon the extent of the first and second mixing effects. Preferably, the first and second mixers abut to ensure that the fluid (22) is mixed continuously as it flows from the first point (30) to the second point (32).

In the preferred embodiment, it has been found that the placement of the conduit (24) in other than a substantially horizontal orientation reduces the gravitational segregation of the fluid (22) by the mixer (34). Thus, the first point (30) and the second point (32) in the conduit (24) are preferably located at different elevations from the horizontal such that the longitudinal axis of the conduit (24), extending between the first and second points (30, 32), is not substantially horizontal. Most preferably, the longitudinal axis of the conduit (24) is substantially vertical. In other words, the first and second points (30, 32) are aligned such that the fluid (22) flows substantially vertically from the first point (30) to the second point (32). In the preferred embodiment, the first point (30) may be either above or below the second point (32) in the conduit (24) depending upon the composition of the fluid (22). If the fluid (22) is a liquid continuous medium, the first point (30) is preferably below the second point (32) in the conduit (24) so that the fluid (22) flows upwards in the conduit (24), and thus follows the tendency of the gas phase or phases to rise. If the fluid (22) is a gas continuous medium, the first point (30) is preferably above the second point (32) in the conduit (24) so that the fluid (22) flows downwards in the conduit (24), and thus follows the tendency of the liquid phase or phases to fall.

The volumetric flow rate determining means of the apparatus (20) may be comprised of any known device, or combination of two or more devices, for determining volumetric flow rate which is compatible with, and suitable for, the specific nature and properties of the fluid (22) being measured. Further, as the fluid (22) is substantially homogeneous at the first location (36) where the volumetric flow rate is determined, the volumetric flow rate determining means is preferably comprised of any known device, or combination of two or more devices, able to relatively accurately measure the volumetric flow rate of a single phase fluid. However, as a single phase fluid may be comprised of either a liquid phase or a gas phase, the specific device used must again be compatible with, and suitable for, the specific nature and properties of the homogeneous fluid being measured.

In the preferred embodiment, the fluid (22) has a flow pattern at the first location (36) in the conduit (24) which causes a pressure drop of the fluid (22) at the first location (36). As a result, the preferred volumetric flow rate determining means is comprised of a measuring device (40) for measuring the pressure drop of the fluid (22) at the first location (36). Thus, the measuring device (40) must be capable of measuring the range of the magnitude of the pressure drop anticipated at the first location (36).

The flow pattern causing the pressure drop is preferably created by the mixer (34). Thus, in the preferred embodiment, the measuring device (40) measures the pressure drop across the mixer (34) at the first location (36). The first location (36) is not a single point or place in the conduit (24), but rather, a physical distance or amount of space between two points or places. In the preferred embodiment, the mixer (34) substantially extends from the first to the second ends (26, 28) of the conduit (24) and therefore extends between the points or places in the conduit (24) defining the first location (36). Thus, the measuring device (40) measures the pressure drop across the portion of the mixer (34) located at the first location (36) or located between the points or places in the conduit (24) defining the first location (36). In the preferred embodiment, the magnitude of the anticipated pressure drop at the first location (36) will vary depending upon the nature and composition of the multi-phase fluid (22) and the specific mixer (34) being used.

In the preferred embodiment, the measuring device (40) is comprised of a conventional differential pressure device located at the first location (36) which measures directly the difference in pressure between the two points defining the first location (36). Alternatively, a first pressure gauge or tap (not shown) and a second pressure gauge or tap (not shown) at the first location (36) could be used in order to make two separate pressure measurements at the first location (36) which can then be compared to each other to determine the pressure drop. This embodiment, however, tends to provide a less accurate measurement of pressure drop than does a differential device. However, as indicated, the measuring device (40) may be comprised of any other suitable known device for measuring the pressure drop of the fluid flow at the first location (36). The pressure drop is then used to determine the volumetric flow rate of the fluid (22) at the first location (36).

Although the flow pattern of the fluid (22) which causes the pressure drop is preferably created by the mixer (34), it may alternately be created by the volumetric flow rate measuring device (40), which is located at the first location (36). Thus, the volumetric flow rate measuring device (40) measures the pressure drop across the measuring device (40) at the first location (36). In this case, the measuring device (40) may be comprised of an orifice, a venturi, a nozzle or a similar measuring device (not shown) positioned at a gap in the mixer (34) at the first location (36). As indicated above, where a gap exists in the mixer (34), the gap must be small enough to permit the upstream and downstream mixing effects to act together to result in a continuous mixing of the fluid (22) through the gap and thus, through the measuring device (40). These types of measuring devices typically result in large pressure drops and therefore their use may not be desirable in some circumstances depending upon the other operating parameters and conditions of the apparatus (20) and the fluid (22).

The density determining means may be comprised of any known density measuring device (44), or combination of devices, compatible with, and suitable for, the specific nature and properties of the fluid (22) being measured. Further, as the density determining means is measuring the density of a homogeneous fluid in the preferred embodiment, the density determining means is preferably comprised of any known device, or combination of devices, able to relatively accurately measure the density of a single phase fluid. However, as a single phase fluid may be comprised of either a liquid phase or a gas phase, the specific device used must again be compatible with, and suitable for, the specific nature and properties of the homogeneous fluid being measured.

As described previously, the density measuring device (44) determines the density of the fluid (22) at the second location (42) in the conduit (24). The second location (42) is located between the first and second points (30, 32) within the portion of the conduit (24) containing the mixer (34). Therefore, the fluid (22) at the second location (42) is substantially homogeneous. In contrast to the first location (36) which is a physical distance between two points or places, the second location (42) may be either a single point or place in the conduit (24) or a physical distance or amount of space between two points or spaces in the conduit (24). Further, the second location (42) may be contiguous or coincident with the first location (36).

Although all of the dimensions of the apparatus (20) should be designed in order to achieve the desired results as set out herein, it has been found that as a general rule of thumb, or starting point for the design of the apparatus (20), the following mathematical relationships to the diameter of the conduit (24) may apply. The minimum length of the conduit (24) between the first and second ends (26, 28) may be about thirty times the diameter of the conduit (24). The distance between the two points or places in the conduit (24) defining the first location (36) may be about twenty to twenty-five times the diameter of the conduit (24). The distance between the first end (26) of the conduit (24) and the first location (36) (i.e. the upstream point or place defining the start of the first location (36)) may be about fifteen times the diameter of the conduit (24). Finally, the second location (42) may be a distance of about three to four times the diameter of the conduit (24) upstream of the downstream point or place defining the end of the first location (36).

The density measuring device (44) may be comprised of an on-line or off-line density measuring device such as a capacitance densitometer, a neutron attenuation densitometer and a nuclear radiation or gamma densitometer. However, in the preferred embodiment, the density measuring device (44) is comprised of an on-line density measuring device in order that the measurement will be continuous. The preferred on-line density measuring device (44) is comprised of a nuclear radiation or gamma densitometer. Further, a dual energy gamma densitometer may be used in order that both the density and the composition of the fluid (22) may be determined.

When using a nuclear radiation or gamma densitometer (44), the apparatus (20), and in particular the conduit (24) and the mixer (34), may need to be adapted to minimize any interference with the measurement of the density by the nuclear radiation or gamma densitometer (44). For instance, in the preferred embodiment, to minimize interference by the conduit (24), which is preferably comprised of a steel pipe, the conduit (24) defines a window (46) at the second location (42) of a sufficient size to allow the nuclear or gamma radiation to pass therethrough without contacting the conduit (24). The window (46) is sealed to prevent the escape of any fluid (22) out of the conduit (24) through the window (46). The window (46) is sealed with a material, such as a beryllium laminated plastic, which will not substantially interfere with the nuclear or gamma radiation. Generally speaking, the presence of metal in the conduit (24) may interfere with the nuclear radiation or gamma densitometer (44). Although a sealed window (46) is preferred, alternately, other adaptations may be made which similarly minimize the interference of the conduit (24) with the measurement of the density by the densitometer (44), such as construction of the entire conduit (24) out of a non-interfering material.

Similarly, the ellipsoidal bodies (38), or other packing material, contained in the conduit (24) are preferably comprised of material which will minimize the interference of the ellipsoidal bodies (38) with the measurement of the density. Thus, the ellipsoidal bodies (38) are comprised of a non-metallic material with negative absorptivity to nuclear and gamma type radiation. In the preferred embodiment, the ellipsoidal bodies (38) are comprised of plastic.

Finally, the apparatus (20) may be further comprised of, or used in conjunction with, a fluid composition analyzer (not shown) for analyzing the composition of the fluid (22). Any known on-line or off-line fluid composition analyzer may be used to determine the composition of the fluid (22) as long as it is compatible with, and suitable for, the specific nature and properties of the fluid (22) being analyzed. However, an on-line fluid composition analyzer is preferred. Alternatively, a separate fluid composition analyzer will not be required in the event that a dual energy gamma densitometer (44) is used, which can determine both the density and the composition of the fluid (22).

The method of the within invention characterizes the flow of the multiphase fluid (22) as the fluid (22) flows through the conduit (24). Preferably, the method is conducted or performed using the apparatus (20) described above. As indicated previously, the specifications and parameters of the preferred embodiment of the apparatus (20) are designed to accommodate, and be compatible with, the flow rate of the fluid (22), the composition and other characteristics of the fluid (22) and the desired pressure drop in the apparatus (20). Further, in order to maintain the accuracy of the apparatus (20), the apparatus (20) should be calibrated before use.

In the method, the fluid (22) is characterized as it flows from the first end (26) to the second end (28) of the conduit (24). Thus, the apparatus (20), and specifically the conduit (24), must be connected into a flow of the multi-phase fluid (22), such as a pipeline, so that the fluid (22) flows through the conduit (24) from its first end (26) to its second end (28). The method for characterizing the fluid (22) flow is comprised of the steps of mixing the fluid (22) as it flows from the first end (26) to the second end (28) such that the fluid (22) is substantially homogeneous at the first point (30) in the conduit (24) and such that the substantial homogeneity of the fluid (22) is maintained between the first point (30) and the second point (32) in the conduit (24). Further, the method is comprised of determining at least one of the volumetric flow rate of the substantially homogenous fluid (22) at the first location (36) and the density of the substantially homogeneous fluid (22) at the second location (42). Preferably, the determining step determines both the volumetric flow rate and the density of the substantially homogeneous fluid (22).

Further, preferably, the mixing step is comprised of continuously mixing the fluid (22) as it flows from the first to the second ends (26, 28). As the first and second locations (36, 42) are located in the conduit (24) between the first and second points (30, 32), the mixing of the fluid (22) and the characterization of the fluid (22) by the determining step are performed simultaneously or concurrently.

The mixing step is comprised of directing the fluid (22) through the mixer (34) in the conduit (24), as described above, to produce the substantially homogeneous fluid (22). Thus, in the preferred embodiment, the mixing step is comprised of disrupting the flow of the fluid (22) through the conduit (24) by directing the fluid (22) through the packing material in the conduit (24), preferably being a plurality of hollow, permeable ellipsoidal bodies (38).

The volumetric flow rate determining step is preferably comprised of the steps of measuring the pressure drop of the fluid (22) at the first location (36), which pressure drop is caused by the flow pattern of the fluid (22) at the first location (36), and using the pressure drop to determine the volumetric flow rate of the fluid (22) at the first location (36). In the preferred embodiment, the flow pattern is created by the mixer (34). Therefore, the measuring step is comprised of measuring the pressure drop across the mixer (34) at the first location (36). The volumetric flow rate measuring step is performed by the volumetric flow rate measuring device (40) described above. Alternately, if the flow pattern is created by the measuring device (40), the measuring step is comprised of measuring the pressure drop across the measuring device (40) at the first location (36).

Once the pressure drop is measured, the pressure drop is used to determine the volumetric flow rate either by applying a theoretical, mathematical model or equation defining the relationship between the pressure drop and the volumetric flow rate for the specific fluid flow or by applying empirical test data defining the relationship between the pressure drop and the volumetric flow rate for the specific fluid flow. Preferably, calibration test data on the fluid flow should be obtained for the apparatus (20) as such data tends to be more accurate due to the limitations of the mathematical model to take into account the flow phenomenon of the particular apparatus (20) being used.

Although the volumetric flow rate determining step is preferably comprised of the steps noted above, this step may be comprised of any known process, or combination of processes, suitable for the specific nature and properties of the fluid (22) being measured. Further, as the volumetric flow rate is being determined for a substantially homogeneous fluid, the volumetric flow rate determining step may be comprised of any known process, or combination of processes, able to relatively accurately determine the volumetric flow rate of a single phase fluid as long as it is compatible with, and suitable for, the specific nature and properties of the homogeneous fluid being measured. For instance, the volumetric flow rate determining step may be performed using a cross-correlation technique at the first location (36). Cross-correlation techniques involve the correlation of the fluctuations of any property in the flowing fluid (22) between two points.

The density determining step is preferably performed by using the density measuring device (44) described above. However, this step may be comprised of any known process, or combination of processes, for determining density which is suitable for the specific nature and properties of the fluid (22) being measured. Further, as the density is being determined for a substantially homogeneous fluid, the density determining step may be comprised of any known process, or combination of processes, able to relatively accurately determine the density of a single phase fluid as long as it is compatible with, and suitable for, the specific nature and properties of the homogeneous fluid (22) being measured.

In the preferred embodiment, in order to facilitate the mixing and determining steps, the first and second points (30, 32) in the conduit (24) should be maintained at different elevations throughout the steps. Particularly, if the fluid is comprised of a liquid continuous medium, the first point (30) in the conduit (24) should preferably be below the second point (32) throughout the mixing and determining steps. Conversely, if the fluid (22) is a gas continuous medium, the first point (30) in the conduit (24) should preferably be above the second point (32) throughout the mixing and determining steps. In either case, the first and second points (30, 32) are preferably aligned such that the fluid (22) flows substantially vertically from the first point (30) to the second point (32).

Further, the method is preferably further comprised of the step of combining the density of the fluid (22) with the volumetric flow rate in order to determine the mass flow rate for the fluid (22). Any known techniques for using the density and the volumetric flow rate to determine the mass flow rate may be used.

Finally, the method may be further comprised of the steps of determining the composition of the fluid (22) and combining the composition with the density of the fluid (22) to determine the flow rate of each constituent element of the fluid (22). Any known methods or techniques for determining the fluid composition may be used as long as it is compatible with, and suitable for, the specific nature and properties of the fluid (22) being analyzed. Further, any known methods or techniques for combining the composition with the density to determine the flow rate of the constituent elements of the fluid (22) may be used.

The embodiments of the invention in which an exclusive property or privilege is claimed are defined as follows:

1. A method for characterizing the flow of a multi-phase fluid as the fluid flows through a conduit from a first end of the conduit to a second end of the conduit, the method comprising the steps of:
   (a) mixing the fluid continuously as it flows from the first end to the second end of the conduit such that the fluid is substantially homogeneous at a first point in the conduit and such that the substantial homogeneity of the fluid is maintained between the first point and a second point in the conduit, wherein the first point and the second point are located between the first end of the conduit and the second end of the conduit; and
   (b) determining at least one of a volumetric flow rate of the substantially homogeneous fluid at a first location in the conduit between the first point and the second point and a density of the substantially homogeneous fluid at a second location in the conduit between the first point and the second point.

2. The method as claimed in claim 1 wherein the mixing step is comprised of directing the fluid through at least one in-line mixer located in the conduit to produce the substantially homogeneous fluid at the first point and to maintain the substantial homogeneity of the fluid between the first point and the second point.

3. The method as claimed in claim 2 wherein the in-line mixer is comprised of a static mixer.

4. The method as claimed in claim 3 wherein the static mixer extends substantially between the first end of the conduit and the second end of the conduit.

5. The method as claimed in claim 4 wherein the static mixer is comprised of the conduit containing a packing material for disrupting the flow of the fluid through the conduit.

6. The method as claimed in claim 5 wherein the packing material is comprised of a plurality of permeable ellipsoidal bodies.

7. The method as claimed in claim 6 wherein the volumetric flow rate determining step is comprised of the steps of:
   (a) measuring a pressure drop of the fluid at the first location in the conduit, wherein the fluid has a flow pattern at the first location which causes the pressure drop; and
   (b) using the pressure drop at the first location to determine the volumetric flow rate of the fluid at the first location in the conduit.

8. The method as claimed in claim 7 wherein the flow pattern of the fluid is created by the static mixer and wherein the pressure drop measuring step is comprised of measuring the pressure drop across the static mixer at the first location.

9. The method as claimed in claim 6 wherein the first point in the conduit and the second point in the conduit are at different elevations throughout the mixing and determining steps.

10. The method as claimed in claim 9 wherein the fluid is comprised of a liquid continuous medium and the first point in the conduit is below the second point in the conduit throughout the mixing and determining steps.

11. The method as claimed in claim 10 wherein the first point and the second point are aligned such that the fluid flows substantially vertically from the first point to the second point.

12. The method as claimed in claim 9 wherein the fluid is comprised of a gas continuous medium and the first point in the conduit is above the second point in the conduit throughout the mixing and determining steps.

13. The method as claimed in claim 12 wherein the first point and the second point are aligned such that the fluid flows substantially vertically from the first point to the second point.

14. The method as claimed in claim 6 wherein the density determining step is performed by using a density measuring device comprised of an on-line density measuring device or an off-line density measuring device.

15. The method as claimed in claim 14 wherein the density determining step is performed using an on-line density measuring device comprising a nuclear radiation or gamma densitometer.

16. The method as claimed in claim 6 wherein the determining step is comprised of determining the volumetric flow rate and the density of the substantially homogeneous fluid and the method is further comprised of the step of combining the density with the volumetric flow rate in order to determine a mass flow rate for the fluid.

17. An apparatus for characterizing the flow of a multiphase fluid, the apparatus comprising:
(a) a conduit having a first end and a second end, for flowing the fluid from the first end to the second end, and a first point and a second point located between the first end of the conduit and the second end of the conduit;
(b) a mixer for mixing the fluid continuously as it flows from the first end to the second end of the conduit such that the fluid is substantially homogeneous at the first point and such that the substantial homogeneity of the fluid is maintained between the first point and the second point in the conduit; and
(c) means for determining at least one of a volumetric flow rate of the substantially homogeneous fluid at a first location in the conduit between the first point and the second point and a density of the substantially homogeneous fluid at a second location in the conduit between the first point and the second point.

18. The apparatus as claimed in claim 17 wherein the mixer is comprised of at least one in-line mixer located in the conduit to produce the substantially homogeneous fluid at the first point and to maintain the substantial homogeneity of the fluid between the first point and the second point.

19. The apparatus as claimed in claim 18 wherein the in-line mixer is comprised of a static mixer.

20. The apparatus as claimed in claim 19 wherein the static mixer extends substantially between the first end of the conduit and the second end of the conduit.

21. The apparatus as claimed in claim 20 wherein the static mixer is comprised of the conduit containing a packing material for disrupting the flow of the fluid through the conduit.

22. The apparatus as claimed in claim 21 wherein the packing material is comprised of a plurality of permeable ellipsoidal bodies.

23. The apparatus as claimed in claim 22 wherein the volumetric flow rate determining means is comprised of a measuring device for measuring a pressure drop of the fluid at the first location in the conduit, wherein the fluid has a flow pattern at the first location which causes the pressure drop.

24. The apparatus as claimed in claim 23 wherein the flow pattern of the fluid is created by the static mixer such that the measuring device measures the pressure drop across the static mixer at the first location.

25. The apparatus as claimed in claim 24 wherein the measuring device is comprised of a differential pressure device located at the first location.

26. The apparatus as claimed in claim 22 wherein the density determining means is comprised of an on-line density measuring device or an off-line density measuring device.

27. The apparatus as claimed in claim 26 wherein the density determining means is comprised of an on-line density measuring device comprising a nuclear radiation or gamma densitometer.

28. The apparatus as claimed in claim 27 wherein the conduit is adapted to minimize interference with the measurement of the density by the nuclear radiation or gamma densitometer.

29. The apparatus as claimed in claim 28 wherein the conduit comprises a sealed window at the second location for minimizing interference by the conduit with the measurement of the density.

30. The apparatus as claimed in claim 29 wherein the ellipsoidal bodies contained in the conduit are comprised of plastic for minimizing interference by the ellipsoidal bodies with the measurement of the density.

* * * * *